United States Patent
Mei et al.

(10) Patent No.: US 8,816,302 B2
(45) Date of Patent: Aug. 26, 2014

(54) OPTICAL ARRANGEMENT AND METHOD FOR EXAMINING OR PROCESSING AN OBJECT

(71) Applicants: Michael Mei, Steinebach (DE); Ronald Holzwarth, Munich (DE); Marc Fischer, Munich (DE)

(72) Inventors: Michael Mei, Steinebach (DE); Ronald Holzwarth, Munich (DE); Marc Fischer, Munich (DE)

(73) Assignee: Menlo Systems GmbH, Martinsried (DE)

( * ) Notice: Subject to any disclaimer, the term of this patent is extended or adjusted under 35 U.S.C. 154(b) by 0 days.

(21) Appl. No.: 13/723,922

(22) Filed: Dec. 21, 2012

(65) Prior Publication Data
US 2013/0161538 A1    Jun. 27, 2013

(30) Foreign Application Priority Data
Dec. 23, 2011   (DE) .................. 10 2011 122 230

(51) Int. Cl.
| G01N 21/31 | (2006.01) |
| B01J 19/12 | (2006.01) |
| G01N 21/64 | (2006.01) |

(52) U.S. Cl.
CPC ....... *B01J 19/121* (2013.01); *G01N 2201/0697* (2013.01); *G01N 21/31* (2013.01); *G01N 21/6402* (2013.01)
USPC ......... 250/492.1; 359/389; 359/385; 359/368

(58) Field of Classification Search
USPC .......... 250/492.1; 359/389, 385, 368; 372/25, 372/30
See application file for complete search history.

(56) References Cited

U.S. PATENT DOCUMENTS

| 4,461,686 | A | * | 7/1984 | Tuccio et al. ............ 204/157.22 |
| 5,034,613 | A | | 7/1991 | Denk et al. |
| 6,108,081 | A | | 8/2000 | Holtom et al. |
| 6,483,735 | B1 | * | 11/2002 | Rentzepis ................ 365/119 |
| 6,785,303 | B1 | | 8/2004 | Holzwarth et al. |
| 6,813,073 | B2 | | 11/2004 | Engelhardt et al. |
| 6,844,963 | B2 | * | 1/2005 | Iketaki et al. ............. 359/368 |
| 7,098,447 | B2 | | 8/2006 | Moellmann |
| 7,804,863 | B2 | | 9/2010 | Adel et al. |
| 8,610,996 | B2 | * | 12/2013 | Krishnamachari et al. ... 359/285 |

(Continued)

FOREIGN PATENT DOCUMENTS

| DE | 199 11 103 A1 | 9/2000 |
| DE | 100 44 404 A1 | 4/2002 |

(Continued)

OTHER PUBLICATIONS

Office Action of the German Patent Office issued in German Application No. 10 2011 122 230.1 dated Aug. 30, 2012 (6 pages).

(Continued)

*Primary Examiner* — Kiet T Nguyen
(74) *Attorney, Agent, or Firm* — Flynn, Thiel, Boutell & Tanis, P.C.

(57) ABSTRACT

The invention relates to an optical arrangement (20) and to a method of examining or processing an object (46). Here, a first laser pulse with a first central wavelength and a second laser pulse with a second central wavelength different from the first central wavelength are generated. Both pulses are superimposed in or on the object (46) such that multi-photon absorption takes place there with the involvement of at least one photon of the first laser pulse and at least one photon of the second laser pulse.

24 Claims, 5 Drawing Sheets

(56) References Cited

U.S. PATENT DOCUMENTS

| | | |
|---|---|---|
| 2002/0063220 A1 | 5/2002 | Engelhardt et al. |
| 2004/0135079 A1 | 7/2004 | Moellmann |
| 2008/0069159 A1 | 3/2008 | Adel et al. |
| 2011/0141540 A1 | 6/2011 | Hochrein et al. |

FOREIGN PATENT DOCUMENTS

| | | |
|---|---|---|
| DE | 100 56 382 A1 | 5/2002 |
| DE | 102 35 914 A1 | 2/2004 |
| DE | 10 2006 023 601 A1 | 11/2007 |
| DE | 10 2008 026 484 A1 | 12/2009 |
| EP | 1 161 782 A1 | 12/2001 |

OTHER PUBLICATIONS

Denk W., Strickler JH, Web WW: "Two-photon laser scanning fluorescence microscopy" in: Science (journal), 248, No. 4951, Apr. 1990, pp. 73-76 (4 pages).

\* cited by examiner

OPTICAL ARRANGEMENT AND METHOD FOR EXAMINING OR PROCESSING AN OBJECT

FIELD OF THE INVENTION

The invention relates to an optical arrangement and to a method for examining an object or processing an object using interaction with pulsed laser light of different wavelengths.

If "multi-photon processes" or "multi-photon interaction" is mentioned in the context of the present invention, processes or interactions with two, three or more involved photons are meant. In particular, two-photon processes consequently are also included in the multi-photon processes within the scope of the invention.

DESCRIPTION OF THE PRIOR ART

The demonstration of two-photon fluorescence microscopy was described for the first time in the article by Denk W., Strickler J H, Web W W: "Two-photon laser scanning fluorescence microscopy" in: Science (journal), 248, No. 4951, April 1990, pages 73-76, a bit later in U.S. Pat. No. 5,034,613. In two-photon fluorescence microscopy, a simultaneous absorption of two photons with identical photon energies (i.e. identical optical frequency or wavelength, respectively) takes place to lift an electron to a higher energy level in an atom or molecule. Optionally after some relaxation, detectable fluorescent radiation is emitted by the atom or molecule containing the electron. Usually, such two-photon processes take place when very short laser pulses are focused into a medium because two-photon absorption quadratically depends on intensity and thus requires very high intensities which can be achieved easiest with pulsed light. In most cases, in two-photon fluorescence microscopy, the substance or sample actually under testing is marked by means of colorants or fluorophores. By selective coupling, one can highly efficiently bind these colorants to the sample. This can be realized, for example, by a chemical or biological lock-and-key principle by the colorants exclusively adhering e.g. to certain cells, e.g. cancer cells, in the sample. By means of an excitation of the colorants via two-photon absorption and a subsequent detection of fluorescence, it is thus possible to indirectly obtain information on the sample, e.g. information on their composition or local distribution. A disadvantage of this conventional two-photon fluorescence microscopy is that the employed laser and the sample or a fluorescence colorant for the sample must be exactly coordinated. With the low number of available laser media, this is a severe restriction. The energy of a single photon is not sufficient for lifting the molecule or atom from its basic state into the excited state. For example, in two-photon absorption, two photons are used at a wavelength of 800 nanometers (nm) to excite a transition at 400 nm.

The advantage of two-photon microscopy over conventional microscopy with the absorption of a single photon are a higher spatial resolution (because, the probability for the simultaneous absorption of several photons is sufficiently high only in the focus), a higher temporal resolution (as a pulsed system is used for illumination), and a deeper penetration depth as photons of a longer wavelength penetrate the media under test to a considerably deeper extent and with less scattering. However, there are also disadvantages compared to conventional microscopy. For example, two-photon microscopy is relatively inflexible as the wavelength of the irradiated laser pulses must match exactly to excite transition. Moreover, the transition probability for two-photon processes is often much lower than for a one-photon process, so that often only low signal emission is available.

Another multi-photon process is sum frequency generation (SFG) which is also employed for sum frequency spectroscopy. In this process, a photon of the sum frequency $f=f_s+f_p$ is generated from a photon with a first frequency $f_s$ and a photon with a second frequency $f_p$, which thus comprises the sum of the energies of both photons. Sum frequency generation is, just as SHG, a non-linear optical process of the second order. It consequently requires an optical non-linear material, i.e. a material with a non-imperceptible susceptibility of the second order $\chi^{(2)}$. Sum frequency mixing can either take place at boundary surfaces or in $\chi^{(2)}$ materials. Its application is therefore limited as it cannot take place directly in material without $\chi^{(2)}$ susceptibility.

Sum frequency mixing is described for its application in non-linear microscopy, for example, in U.S. Pat. No. 6,108,081 A.

SUMMARY OF THE INVENTION

It is the object of the present invention to provide an optical arrangement and a method for examining an object or working on an object which are very flexible as to their application and very precise as to their resolution, and which moreover are subject to as little restrictions as possible in view of the materials to be worked on or examined.

This object is achieved by an optical arrangement having the features of the present invention and by a method having the features of the present invention, and also by the use of such an optical arrangement or such a method for multi-photon spectroscopy, multi-photon fluorescence microscopy or multi-photon material working.

The optical arrangement according to the invention is characterized in that it comprises a first laser pulse generator for generating a first laser pulse with a first central wavelength, and a second laser pulse generator for generating a second laser pulse with a second, different central wavelength. Central wavelength is here either the wavelength of the respective laser pulse with the highest intensity, or else the wavelength at the center of the full width at half maximum (FWHM) of the spectrum of the laser pulse. It should be noted that each laser pulse has a finite spectrum which is the wider (or comprises the more modes) the shorter the pulse is.

The inventive optical arrangement furthermore comprises a beam steering system which is configured to superimpose the first laser pulse and the second laser pulse at a certain target position in or on the object such that multi-photon absorption takes place at the target position with the involvement of at least one photon of the first laser pulse and at least one photon of the second laser pulse, i.e. at least two-photon absorption with two photons of different energies or frequencies or wavelengths. Such two- or multi-photon absorption will take place if the material of the object comprises an energy level at the target position whose energy difference to a basic level corresponds to the sum of the photon energies of the two laser pulses.

The object can be a workpiece or a sample of organic or inorganic, normally transparent materials, for example a biological sample or plastics. In particular with biological samples, special colorant or marking molecules can be employed for intensifying the effect, i.e. the samples are marked with one or several colorants. Here, the object should be preferably transparent both for the radiation of the first laser pulse and for the radiation of the second laser pulse to minimize losses of radiation before the target position is reached. The beam steering system can comprise an arbitrary number and array of different optical elements, such as mirrors, beam splitters, beam combiners, lenses and lens systems and apertures.

The advantage of the optical arrangement according to the invention compared to conventional sum frequency mixing primarily consists in the inventive multi-photon interaction not being restricted to the surface or boundary surfaces of the object, but also being capable of taking place inside the object (i.e. in the bulk of the object) independent of the existence of boundary surfaces of different material regions or a second order susceptibility. Moreover, the photon momentum conservation in the optical arrangement according to the invention is fulfilled in a simple manner analogously to the degenerated two-photon interaction. In conventional sum frequency mixing, however, photon momentum conservation leads to the restriction that the light with sum frequency could only be observed at a very small solid angle and the two basic frequencies compulsorily had to be filtered out.

Compared to the conventional "degenerated" two-photon absorption with the absorption of two photons of identical energies, however, the particular advantage of the invention consists in an immense variety of new interactions between laser radiation and the material of the object being permitted, which can be utilized for obtaining new information on the object and its material. Moreover, in the interaction according to the invention, the probabilities of a transition of the material from the basic state to the excited state can be changed by changing the parameters of laser radiation. In particular, the transition probability can be clearly increased compared to a conventional "degenerated" two-photon absorption. In many fluorophores, by the interaction generated by the optical arrangement according to the invention, transitions can be excited which could not be obtained up to now and can initiate new processes in the objects to be examined or worked on.

In a first variant of the invention, as a first laser pulse generator and a second laser pulse generator, one pulsed laser each is provided, these two pulsed lasers being synchronized with each other, for example, by electronic measures. It is here suitable for the so-called "jitter", i.e. the fluctuation or variation in time of the cycle times of the lasers, to be within the range of the pulse durations of the two lasers or even below it. For example, the one laser could be an erbium-doped fiber laser, the other one could be an ytterbium-doped fiber laser.

In this first variant of the optical arrangement according to the invention, two (or more) laser pulses of often different wavelengths are not generated by one common laser but by two (or more) lasers. This broadens the field of application as all wavelengths of femto-second lasers are thus possible and thus many of the current colorants and transitions can be excited. At least one of the lasers should comprise an actuator controlled by a synchronization device for varying the pulse repetition rate as in this case, the laser pulses from the different lasers should be synchronized by means of electronic methods, so that the overlap in time of the laser pulses in the sample or at the object is ensured over a relatively long period. In case of two lasers, this can be realized, for example, by an Er-doped femto-second fiber laser and an Yb-doped femto-second fiber laser which are synchronized to a common radiofrequency (or one fs laser is the "master" and the other one is the "slave" laser, i.e. one of them is synchronized to the other one). Here, synchronization must be at least good enough for portions of the pulses to overlap in time in the sample or at the object. The radiofrequency can be generated e.g. by an independent, highly stable quartz, or else be derived from the pulse repetition rate of a laser.

Stabilization is accomplished via a so-called phase locked loop. As an actuator in the laser resonant cavity, a piezo actuator is generally used which is mounted behind or at one of the mirrors of the laser resonant cavity. However, in addition or as an alternative, an electro-optic modulator in the laser resonant cavity or a stepper motor which moves one of the cavity mirrors, or a combination of these actuators can be employed.

For detection, a cross-correlation method can also be employed. Here, the pulses of the two lasers are superimposed in a non-linear crystal and the sum frequency is generated. This constitutes a very sensitive detector for the position of the pulses with respect to each other in time. The signal of cross-correlation is then supplied to the synchronization device as an input signal.

In another variant of the invention, a common pulsed laser is provided for the first laser pulse generator and the second laser pulse generator, the one laser pulse generator being configured to change the central wavelength of a primary laser pulse from the pulsed laser, for example shift it, by an amount different from that of the other laser pulse generator. It would in particular also be conceivable to change the central wavelength only of the one laser pulse, but not of the other one. In this variant, the primary laser pulse of the pulsed laser, for example of a frequency comb or an ultra-short pulse laser, is divided into two secondary parts by means of a beam splitter. Now, the central wavelength of the one laser pulse can be changed, for example by self-phase modulation, by $2^{nd}$ or $3^{rd}$ Harmonic Generation (SHG, THG), or by a Raman shift, as is described, for example, in DE 10 2006 023 601 A1. After this frequency shifting, the two secondary parts of the laser pulse can be superimposed again, at the latest at the target position in the object. In this variant, the two secondary parts of the laser pulse are even largely coherent with respect to each other.

The beam steering system can be configured such that the first laser pulse and the second laser pulse are superimposed at the target position entirely, or only partially. The smaller the spatial overlap between the two laser pulses is, the higher is the spatial resolution when examining or processing the object. It is possible that the spatial overlap between the two laser pulses is as small as one femtoliter, or smaller. It is also conceivable that the degree of spatial overlap between the two laser pulses is variable, for example in order to vary the spatial resolution.

In still another variant of the invention, a common pulsed laser is also provided for the first laser pulse generator and the second laser pulse generator, the one laser pulse generator being configured to filter out a spectral region from the primary spectrum of the pulsed laser of another central wavelength than the other laser pulse generator. Here, too, for example a frequency comb generator can be used as a common pulsed laser as it is known from DE 199 11 193 A1, EP 1 161 782 81, or DE 100 44 404 C2, the disclosure of which is hereby incorporated by reference. As frequency comb generator, one short-pulse or ultrashort-pulse oscillator each is provided in this situation, i.e. a mode-coupled laser with pulse durations within a range of femto—(fs) to nanoseconds (ns). A "frequency comb" corresponds to the sequence of laser pulses in the frequency space. It is composed of a plurality of sharp, δ-like functions at different discrete frequencies, referred to as modes $f_n$. Mathematically, the frequency comb can be described as $f_n = f_0 + n\Delta f$. Here, $f_0$ is the so-called offset frequency, $\Delta f$ the frequency distance of adjacent modes corresponding to the inverse of the cavity round-trip time. After a division of the primary laser pulse of the pulsed laser by a beam splitter, in one or in both of the two paths, spectral filtering could take place which permits only certain modes of the frequency comb to pass. As a result, two secondary laser pulses with different central wavelengths would be available.

If a common pulsed laser is used, it is particularly advantageous regarding the efficiency of the examination or processing of the objects if the common pulse laser is a frequency comb generator. Phase coherent supercontinua, such as the output of frequency comb generators, allow the filtering into different colors of the laser light, thereby allowing to achieve very short pulses.

Preferably, the first laser pulse and/or the second laser pulse is/are an ultra-short laser pulse, i.e. a sub-picosecond laser pulse, i.e. a laser pulse with a duration of less than one picosecond (ps). These pulses are characterized, apart from by their short duration, by their high peak intensity which clearly increases the probability for the multi-photon absorption aimed at, compared to longer pulses. If a lower probably is sufficient, however, one or both of the laser pulses could also be replaced by a laser pulse of a longer duration, or in an extreme case even by light of a continuous wave optical laser (CW laser).

It is suitable for the beam steering system to comprise first focusing optics for focusing the first laser pulse to the target position and/or second focusing optics for focusing the second laser pulse to the target position. These focusing optics increase the intensity of the laser pulses at the target position and thus increase the probability for the multi-photon absorption aimed at. At the same time, they reduce the beam cross-section and thus increase resolution. Additionally or as an alternative, common focusing optics could also be provided for both laser pulses.

The optical arrangement can furthermore comprise a detector for signal emission. This signal emission can comprise photons whose energy corresponds to the sum of a photon of the first laser pulse and a photon of the second laser pulse—or which is slightly below the sum of these energies if signal emission is emitted only after a certain relaxation into a state with a somewhat lower energy above the basic state. A filter, for example a band-pass filter, could also be allocated to the detector to let the signal emission pass and suppress noise and/or the two fundamental wavelengths. It would moreover be conceivable for the detector to be a confocal detector, that means which rejects radiation from areas of the object offside the target position illuminated by the two laser pulses.

Particular advantages arise if the first laser pulse generator and/or the second laser pulse generator are tunable, i.e. if the central wavelength of the laser pulses generated by them can be continuously varied, if possible. This permits to either continuously change the sum of the photon energies, or to change the contribution the individual photons make to a predetermined total energy. In this manner, additional information on the material of the object can be gained, or intermediate levels or virtual intermediate levels in the material can be utilized to change, in particular increase, the probability for multi-photon absorption.

In any embodiment of the invention, an optional dispersion controller allowing to compensate for material and waveguide dispersion can be configured such that the first laser pulse and the second laser pulse are superimposed as short pulses in time at the target position entirely, or only partially. The shorter the pulses are and the better the overlap in time at the target is the stronger are the non-degenerate two-photon absorption and the detected signal of the subsequent emission. The dispersion controller can be implemented e.g. as a fiber setup using fibers with different dispersion parameters (also employing fibers with positive and negative dispersion for the corresponding wavelengths) or also using fiber Bragg gratings. Alternatively, it can consist of free space elements like prisms and/or gratings.

The invention also relates to a method for examining an object or working on an object (i.e. processing an object). In this method, a first pulse with a first central wavelength and a second pulse with a second, different central wavelength are irradiated onto the object such that at a certain target position in or on the object, multi-photon absorption takes place with the involvement of at least one photon of the first laser pulse and at least one photon of the second laser pulse. The different central wavelengths mean that the two photons have different energies.

In the method according to the invention, the first and second laser pulses can be generated either by means of two separate synchronized lasers, or by means of first and second laser pulse generators which generate secondary or second laser pulses each with different central wavelengths from primary laser pulses provided by a common pulsed laser.

The requirement of applying the two laser pulses onto the object such that the desired multi-photon absorption takes place can be particularly well met by the two laser pulses reaching the target position simultaneously or at most at an interval corresponding to half the laser pulse duration (i.e. $\Delta t \leq \frac{1}{2}\, \tau_{FWHM}$; with $\tau_{FWHM}$ as the FWHM laser pulse duration), and/or certain minimum intensities of the two laser pulses are obtained at the target position, for example by suited focusing of the laser radiation. The aim is that the focused laser pulses at least partially overlap in space and time. With this multi-photon absorption of at least two photons of different energies, the advantages already illustrated in detail above are achieved.

In view of the advantages of a use of a sub-picosecond laser pulse for the first and/or second laser pulse and a focusing for the first and/or second laser pulse onto the target position also in the method according to the invention, reference is also made to the above statements.

In an advantageous variant of the invention, a region of the object is sampled, i.e. scanned, by changing the target position. This permits to not only examine or change one single target position of the object, but larger regions of the object in view of their material properties. Changing the target position can be performed by the object lying on a sample table or in a mounting and being moved translationally and/or rotated in one or several directions in space. As an alternative to this, a scanner arrangement with one or several scanner mirrors could be provided which deflect one or both laser beams of the first or the second laser pulse over the object.

If it is desired to vary the overlap of the laser pulses in time and/or the location of the target position where the two laser pulses overlap, there are many possibilities available for this. One variant consists in the so-called Asynchronous Optical Sampling (ASOPS) of the two laser beams. In particular during the adjustment of the optical arrangement according to the invention, a certain temporal range can be driven through to find the working point where the pulses are at least partially overlapped in time. With the ASOPS method, the conventional mechanical delay line in the one arm of the construction is replaced by a sampling method which does not require any mechanical delay line. This is realized by stabilizing two (or more) lasers with different pulse repetition rates with respect to each other. It is an advantage that this merely optical sampling can be performed quasi at any desired speed. By this, effects which origin from pulses shifted with respect to each other in time can also be easily and quickly examined.

Another variant consists of the so-called OSCAT method (Optical Sampling by Cavity Tuning, abbr. OSCAT) which is known from DE 10 2008 026 484 A1, the disclosure of which is hereby incorporated by reference. In this OSCAT method, two laser pulses are irradiated into one common or two different target positions, the first pulse directly reaching a first target position and the second pulse reaching a second target region after it has passed a delay line. It is moreover possible to adjust the delay of the two laser pulses in the respective target region via the pulse repetition rate of the pulsed beam. The optical arrangement according to the invention with one laser and two passive beam control paths of different lengths (in most cases realized by means of glass fibers) can ensure optical sampling by periodic variation of the pulse repetition rate of the laser and thus realize similar advantages of the ASOPS method in the application. It can prove to be advantageous that here only one short-pulse laser must be used.

A variant of the method where the first and/or the second central wavelength are changed furthermore presents essential advantages. This permits the changing of the sum of energies of the photons coming from both laser pulses to excite other energy transitions in the material of the object. As an alternative, the sum of the photon energies could also be kept constant, while simultaneously the first and the second central wavelengths are changed in opposite directions to change the contribution of the photons of the two laser pulses to the total energy. Here, the probability for the simultaneous absorption of two photons in the material of the object could change depending on whether and at what energies intermediate levels or virtual intermediate levels are present in the energy spectrum of the material of the object.

In still another variant of the method, the distance in time between the arrival of the two first and second laser pulses at the target position can be changed, and/or the intensity of the two laser pulses could be changed. One can also obtain information on the material of the object from these changes and the changes resulting therefrom in the signal light emitted by the object and subsequently detected.

The optical arrangement according to the invention or the method according to the invention can preferably be used for multi-photon spectroscopy, multi-photon fluorescence microscopy of the object, or for multi-photon material processing. In multi-photon spectroscopy, information on the reaction of the object are obtained at given or varied combinations of central wavelengths of the two laser pulses, in particular, information on the probability for a multi-photon excitation of the material of the object to obtain in this manner information on the material properties of the object. In multi-photon fluorescence microscopy, a local or large-surface (scanned) excitation of the object or a sample takes place by multi-photon absorption. Subsequently, fluorescent light from the sample is detected whose photon energy approximately corresponds to the sum of photon energies of the original laser pulses. So, the optical arrangement can be integrated in a (fluorescence) microscope, in particular into a laser scanning microscope.

As an example for multi-photon material processing with the method according to the invention, e.g. multi-photon polymerization of a workpiece offers itself. In the process, a certain polymer is excited and cured by multi-photon absorption. This effect can also be obtained if a photosensitizer, such as riboflavin, is placed into a biological sample which is subsequently treated by the method according to the invention. As an alternative, multi-photon material processing could also comprise a local heating of the object up to an optical breakthrough with cavitation bubble formation which could be used for a local cutting of the object.

The optical arrangement according to the invention and the method optionally furthermore comprise methods for the optimized excitation by utilizing the polarization of the exciting light. For example, the first laser pulse can have a linear polarization, and the second laser pulse can have a polarization which is perpendicular to it and also linear. By this, for example an advantageous spatial superimposition of the laser pulses by means of polarization-dependent optical elements can be effected. Equally, polarizations differing from linear polarization can be used (e.g. elliptic polarizations) to utilize advantageous effects of excitation.

Such polarization effects can also be employed on the side of detection. For example, polarization-dependent filters can be employed to increase the suppression of the exciting light from the signal.

The polarization of the incident optical radiation can be parallel or perpendicular, or be in any arbitrary other relation to the molecular dipole moment of the biological samples. The coupling will correspondingly be stronger or weaker. This permits the making of a statement on the orientation of the molecules in the biological samples. The use of two central wavelengths with two polarization vectors for optical excitation here offers completely new possibilities.

In general, there is a polarization dependence of the optical contrast and a polarization dependence of optical processes, such as in two-photon absorption or non-linear coherent effects which can supply statements on the orientation of molecules in biological samples.

The property of the coherence of laser pulses plays a decisive role in many applications, e.g. in the already mentioned optical frequency combs. In the optical arrangement according to the invention, non-coherent as well as coherent light pulses can be used. In the case of coherent light pulses, new fields of application of the optical arrangement according to the invention present themselves. The coherent properties of the light pulses permit the utilization of quantum-mechanical properties, in particular the coherent manipulation of transition probabilities. By a precisely adapted sequence of coherent light pulses, a more efficient excitation can be effected, and new effects can occur. By the use of at least one pulse shaper or (more generally) beam shaper in one or several paths, these effects can even be amplified. Pulse shaping can be performed in multiple ways, e.g. by (but not limited to) liquid crystals assemblies, membranes, devices based on electro- or acousto-optical modulators. By means of a pulse shaper basically an arbitrary train of pulses can be employed which allows for increased flexibility and increased signal strength. The pulse shapers (or beam shapers) can also be employed as variable attenuators or as optical elements which influence the phase of the light pulses. In addition, an optional wavefront sensor can be employed to measure the waveform of the pulses and such further optimize, e.g. by active feedback, the signal strength.

In both the optical arrangement and the method of the present invention, the following additional variations are conceivable:

The two laser pulses may be directed onto the target position from any non-zero mutual angle, i.e. in any non-parallel configuration.

The two laser pulses may alternatively be directed onto the target position from opposite directions.

The mutual angle, from which the first and second laser pulses are directed onto the target position, may be variable.

The degree of spatial overlap between the first and second laser pulses at the target position may be variable.

At the target position, there may be a complete or only a partial spatial overlap between the first and second laser pulses.

At least one optical amplifier, or several optical amplifiers, preferably in the form of a fiber optical amplifier, may be installed at any position along the path of the first laser pulse and/or along the path of the second laser pulse.

BRIEF DESCRIPTION OF THE DRAWINGS

Below, advantageous embodiments of the optical arrangement according to the invention and the method according to the invention will be illustrated more in detail with reference to a drawing. The figures show in detail.

Figure 1:
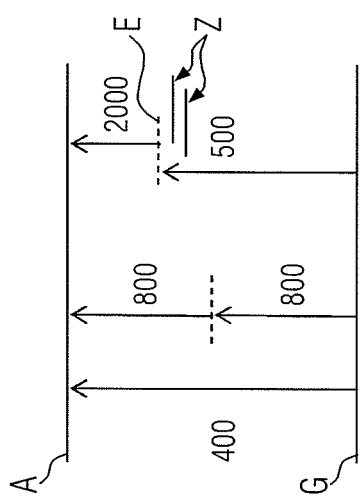
FIG. 1 a schematic representation of an energy diagram of the material of an object to be examined or worked on or of the colorant bound to the material or object, FIG. 2 a conventional optical arrangement for two-photon microscopy, FIG. 3 a schematic representation of an embodiment of an optical arrangement according to the invention during its adjustment, FIG. 4 the optical arrangement represented in FIG. 3 during the examination or working of an object, FIG. 5 a diagram showing possible combinations of photons for a transition at 400 nm, FIG. 6 a representation of possible combinations of photons for a transition at 640 nm, and FIG. 7 a schematic representation of other variants of the optical arrangement.

Equal components are always provided with equal reference numerals in the figures.

DETAILED DESCRIPTION OF THE INVENTION

FIG. 1 schematically shows an energy diagram of the material of an object to be examined or worked on or the colorant bound to the material or object. This material has a characteristic energy transition from a basic state G to an excited state A. The energy difference between these two states of an atom or molecule of the material is $\Delta=A-G=h\nu$, where h is Planck's quantum of action and v is the light frequency. After conversion, this light of frequency v has a wavelength of 400 nm, which is why the band transition is designated with "400" in FIG. 1. One example of such a material is the colorant DY-405 of the Company Dyomics which exhibits an absorption at 400 nm and an emission with a maximum at 423 nm.

In a conventional so-called "degenerated" two-photon absorption, this band transition is bridged by simultaneously absorbing two photons of identical energies or an identical wavelength of 800 nm each.

Figure 2:
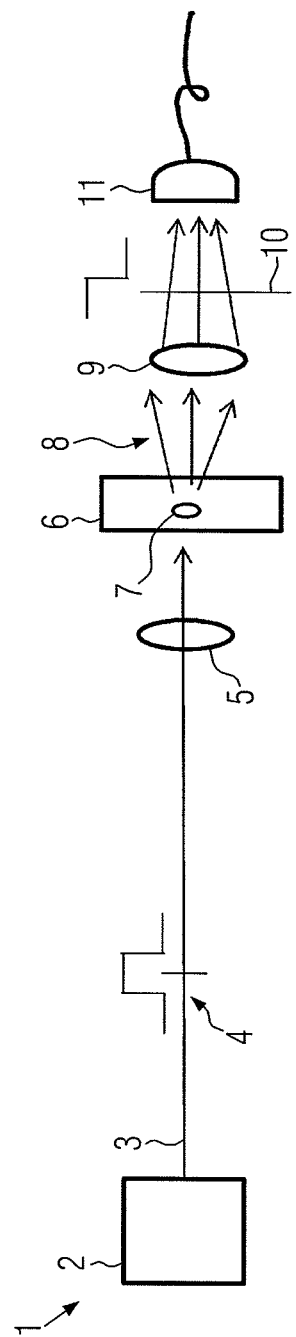

FIG. 2 schematically shows a conventional optical arrangement 1 by which "degenerated" two-photon absorption can be performed. The conventional optical arrangement 1 has a comparatively simple construction. It has an ultra-short pulse laser or a frequency comb generator 2 which emits ultra-short laser pulses of a duration of less than one nanosecond, preferably of less than one picosecond. For example, a FC1500-type frequency comb generator by Menlo Systems GmbH can be used for this. The radiation 3 of the laser 2 is directed over a band-pass filter 4, for example over a band-pass filter 855/210 of the Company Semrock. Beyond the band-pass filter 4, the laser pulses of the laser 2 have a central wavelength of 855 nm at a bandwidth of the filter of 210 nm.

A focusing optics 5 schematically represented as a lens focuses the radiation 3 present in the form of ultra-short laser pulses into an object 6, for example into a (biological) sample. At a target position 7 within the object 6, that is the location of the focus of the focusing optics 5, the two-photon absorption represented in FIG. 1 is effected in which two photons of a wavelength of 800 nm are simultaneously absorbed to perform the energy transition in the material of 400 nm.

From the target position 7, i.e. from the excited region of the object 6, fluorescent radiation 8 is subsequently emitted. If the object 6 is mixed, for example, with the colorant DY-405, it could be fluorescent radiation 8 at a wavelength of 423 nm. Via imaging optics 9 and a detection filter 10, for example a low-pass filter that blocks out primary radiation 3 and lets pass only fluorescent radiation 8, the fluorescent radiation 8 is focused onto a detector 11. Consequently, the fluorescent radiation 8 is the signal emission which is detected by the detector 11. The signal of the detector 11 can be evaluated to obtain, for example, spectroscopic information on the material of the object 6 at the target position 7.

Back to FIG. 1: We can see there that the energy transition from the basic state G to the excited state A is effected in accordance with the invention by a non-degenerated two-photon absorption (or generally by a non-degenerated multi-photon absorption), i.e. by an absorption of photons of different energies or wavelengths, respectively. By way of example, it is indicated in FIG. 1 that a two-photon absorption of a first photon is effected at a wavelength of 500 nm and of a second photon at a wavelength of 2000 nm to altogether excite the 400 nm transition. The photon at a wavelength of 500 nm has a higher energy than the photons of 800 nm used up to now, and in particular a clearly higher energy than the further photon at a wavelength of 2000 nm involved in the two-photon absorption according to the invention. In FIG. 1, moreover intermediate levels (or states) Z between the two energy transmissions G, A are indicated. These intermediate levels Z can also be virtual intermediate levels. The probability for the inventive, non-degenerated multi-photon absorption can highly depend on the existence and position of such intermediate levels Z. It can in particular be enormously increased with respect to the probability of a conventional degenerated multi-photon absorption when the distance of such intermediate levels Z from the basic state G or from the excited state A essentially corresponds to the energy E of a photon involved in the non-degenerated multi-photon absorption.

Figure 3:
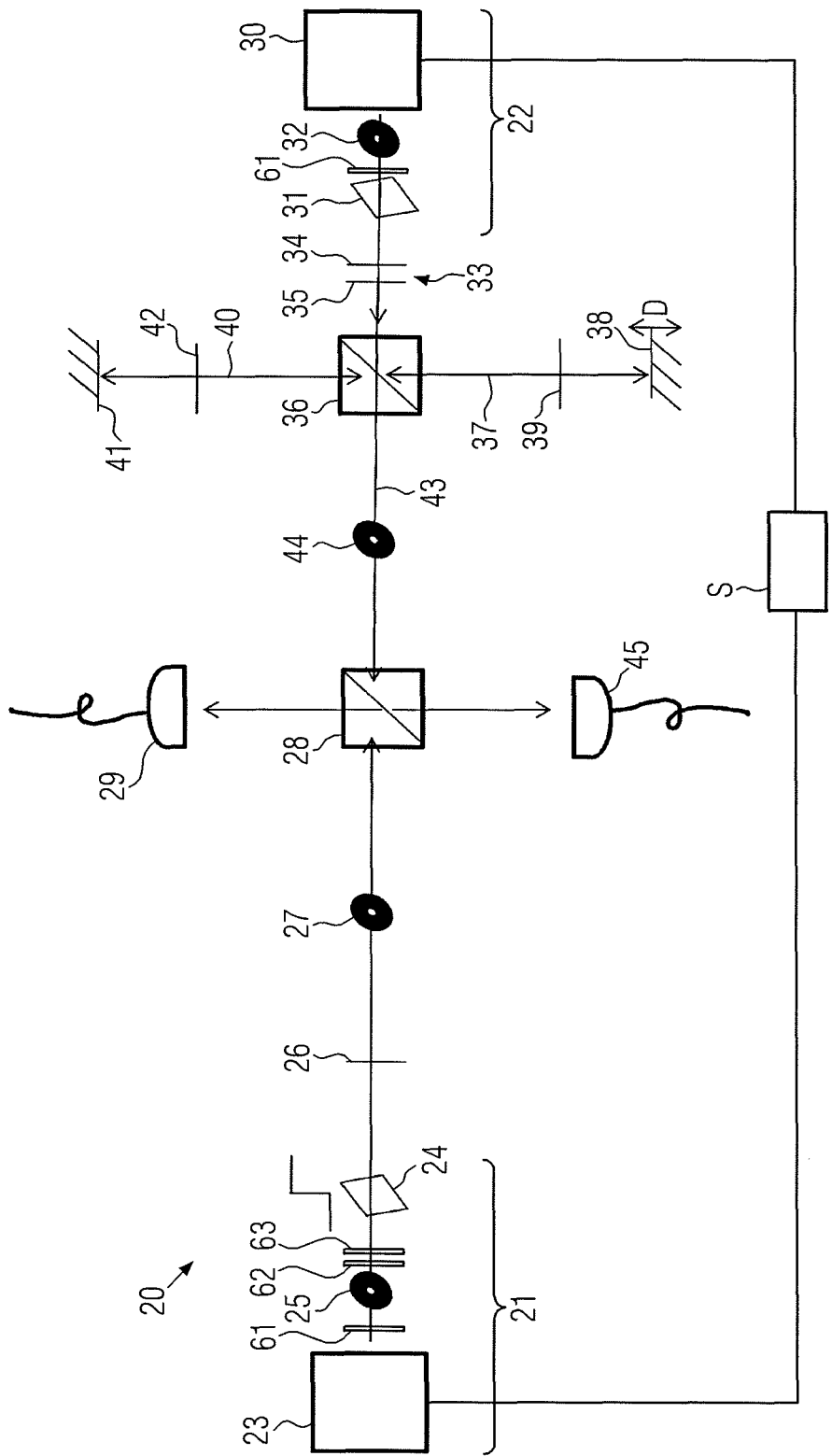

FIG. 3 now shows an embodiment of an optical arrangement 20 according to the invention at a time during its adjustment. The optical arrangement 20 has a first laser pulse generator 21 and a second laser pulse generator 22 which each comprise a group of several optical elements. The first laser pulse generator 21 comprises a sub-picosecond laser or a frequency comb generator 23 which generates laser pulses with a duration of less than one picosecond (ps). For example, an FC1500-type frequency comb generator by Menlo Systems GmbH can be used for this. The first laser pulse generator 21 furthermore comprises an optical filter 24, for example a 1500-, 1750- or 2000-type frequency low-pass filter which each preferably lets pass a radiation of a wavelength of more than 1500 nm, 1750 nm or 2000 nm. Beyond the filter 24, i.e. at the output of the first laser pulse generator 21, the laser pulses generated by this first laser pulse generator 21 consequently have a central wavelength of, for example, 2000 nm. Between the laser 23 and the filter 24, there optionally also is an iris diaphragm 25 to simplify adjustment.

Via a λ/2 plate 26, for example for a wavelength of 2000, and an iris diaphragm 27, the first laser pulses reach a polarization beam splitter (PBS) 28. Conditioned by the polarization of the first laser pulses defined by the λ/2 plate 26, the beam splitter 28 directs them to a first detector 29, which is a photodiode, at an angle of 90°.

The second laser pulse generator 22 also has an ultra-short pulse laser 30, for example a further FC1500-type frequency comb generator by Menlo Systems GmbH. Moreover, the second laser pulse generator 22 also has an optical filter 31. This filter 31, however, is now configured to filter another spectral range from the spectrum of the pulsed laser 30 than the filter 24 from the pulsed laser 23 of the first laser pulse generator 21. For example, the optical filter 31 can be a band-pass filter, e.g. a 512/25-type band-pass filter by the Company Semrock. Thus, the laser pulses leave the second laser pulse generator 22 with a central wavelength of 500 nm. An iris diaphragm 32 is located between the laser 30 and the filter 31.

Behind the second laser pulse generator 22, the second laser pulses 34 generated by the latter pass through a polarization actuator 33 which in turn comprises a λ/2 plate 34 and a λ/4 plate 35 for a wavelength at or near 500 nm, for example optimized for a wavelength of 532 nm. By means of the λ/2 plate 34, the polarization direction of the laser light generated by the second laser pulse generator 22 can be rotated by a selectable angle. By means of the λ/4 plate 35, circularly polarized light becomes linearly polarized light. Together, the elements of the polarization actuator 33 permit to set the polarization of the second laser pulse to an exactly defined value. This value is selected such that the second laser pulses are subsequently deflected into a first path 37 by a polarization beam splitter 36 at an angle of 90°. A mirror or reflector 38, respectively, is located in this first path 37 whose distance D to the beam splitter 36 can be varied. By a change of the distance D, the running time of the second laser pulse in the first path 37 is changed. The first path 37 thus functions as a variable delay line for the second laser pulses.

Between the polarizing beam splitter 36 and the reflector 38, there is another λ/4 plate 39. As it is passed twice, i.e. both on the way there and on the way back, it altogether acts as λ/2 plate and rotates the polarization direction of the second laser pulses by 90°. This leads to the second laser pulses passing the polarization beam splitter 36 losslessly and without deflection and thus reaching a second path 40. Analogously to the first path 37, the second path 40 also has a mirror or reflector 41, respectively, and a λ/4 plate 42 disposed between the mirror 41 and the beam splitter 36. This plate is passed twice by the radiation and thereby rotates the polarization direction again by 90°, so that the second laser pulses are subsequently deflected into a third path 43 by the polarization beam splitter 36 by an angle of 90° where a further iris diaphragm 44 is located for beam shaping. This third path 43 is oriented such that it reaches the polarization beam splitter 28 collinearly and exactly in the direction opposite to the first laser pulses generated by the first laser pulse generator 21. This beam splitter 28 deflects the second laser pulses to a second detector 45 by an angle of 90°. This second detector 45 can be an avalanche photodiode.

The two detectors 29, 45 each have the same distance to the polarization beam splitter 28. This ensures that the first laser pulses from the first laser pulse generator 21 and the second laser pulses from the second laser pulse generator 22 simultaneously reach the beam splitter 28 when they are simultaneously detected on the two detectors 29 and 45, respectively. To detect this, the signals of the two detectors 29, 45 are superimposed on a suited measuring device, for example an oscilloscope, and compared with each other. If there is a difference in time between the arrival of the two laser pulses, this difference in time can now be eliminated by a change of the delay of the second laser pulse. To this end, the distance D of the reflector 38 in the first path 37 to the polarization beam splitter 36 is changed until the two laser pulses simultaneously arrive at the beam splitter 28 and thus at the two detectors 29, 45.

Apart from a determination of the central wave lengths of the two laser pulses, the two optical filters 24, 31 have a further effect: They prevent light from the first laser pulse generator 21 from getting into the cavity of the laser 30 of the second laser pulse generator 22, and vice versa. In this manner, a possibly interfering feedback to the cavities of the two lasers 23, 30 is prevented despite the exactly opposite direction of the two laser pulses.

FIG. 3 furthermore shows a synchronization device S for synchronizing the two lasers 23, 30. The synchronization device S can be an electronic synchronization device which takes care that the two lasers 23, 30 emit laser pulses exactly in time or in precise temporal relation with respect to each other. As an input signal, the synchronization device S can obtain the signal from a cross-correlation between the laser pulses of the two lasers 23, 30.

Figure 4:
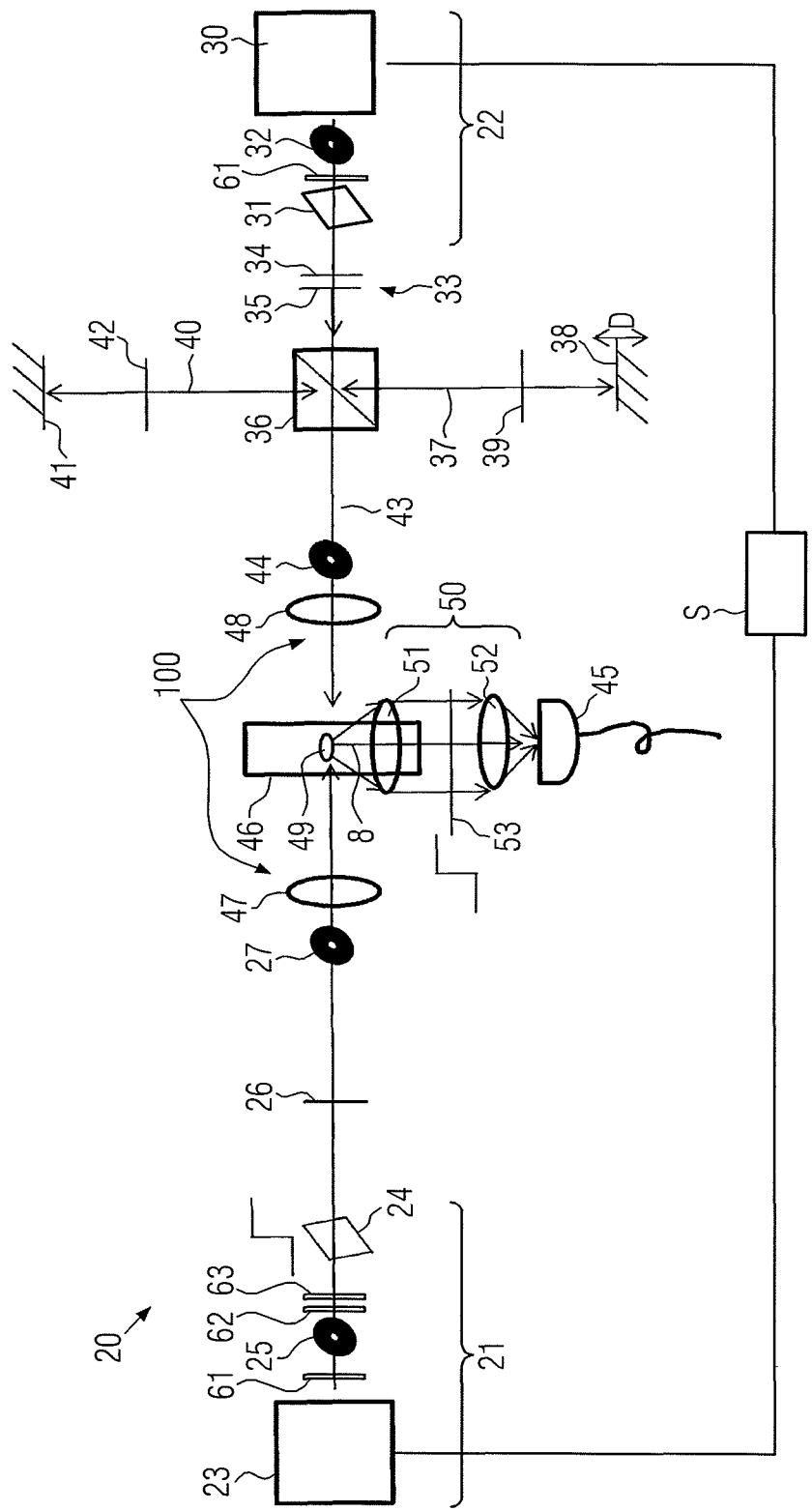

FIG. 4 shows the optical arrangement 20 according to the invention in a condition where it is ready to perform the method according to the invention. After the adjustment illustrated in FIG. 3 has ensured that the first laser pulse and the second laser pulse arrive simultaneously at the location of the polarization beam splitter 28, this beam splitter 28 and the first detector 29 were removed. Exactly at the location of the beam splitter 28, an object 46 to be processed, or in the present case an object 46 to be examined, i.e. a sample, for example a biological sample or a substance of unknown material, has been placed instead. Moreover, first focusing optics 47 for the first laser pulses and second focusing optics 48 for the second laser pulses have been added. These focusing optics 47, 48 can each comprise one or several lenses. They are configured and arranged such that they focus both the first laser pulses generated by the first laser pulse generator 21 and the second laser pulses generated by the second laser pulse generator 22 at a common target position 49 which is within the object 46.

Together, the first focusing optics 47 and the second focusing optics 48 form a beam steering system 100 which is configured to focus the first laser pulse and the second laser pulse to the target position 49 in or on the object 46. The iris diaphragms 27 and 44 can also be added to the beam steering system 100.

Detection optics 50 are provided perpendicularly to the irradiation directions of the two laser pulses which in the present case are designed as a telescope and comprise two lenses 51, 52. The detection optics 50 serve to focus the fluorescent radiation 8 generated by the target position 49 within a maximum possible angle and to direct it to the second detector 45. Between the lenses 51, 52 of the detection optics, or at another location between the object 46 and the second detector 45, there is an optical filter 53, for example a frequency high-pass filter which only lets pass radiation of a wavelength below 700, 600 or 500 nm.

For performing the method according to the invention, the first laser pulse generator 21 and the second laser pulse generator 22 now generate first or second laser pulses which are focused via the focusing optics 47, 48 onto the target position 49 within the object 46. The adjustment of the variable delay of the second laser pulses, i.e. by adjusting the distance D of the reflector 38 from the polarizing emitter 36, ensures that the two laser pulses always reach the target position 49 simultaneously. There, the multi-photon absorption according to the invention takes place where, for example, a photon of the first laser pulse with a wavelength of 2000 nm and a photon of the second laser pulse with a wavelength of 500 nm are simultaneously absorbed to bring together an atom or molecule of the material of the object 46 into an excited state A at the target position 49 with a 400 nm transition.

After some relaxation, the material of the object 46 emits fluorescent radiation 8 from the target position 49 which is focused via the detection optics 50 onto the second detector 45 and detected there. The intensity of the signal emission 8 can here serve as measure for the transition probability and be consulted for findings on the material properties of the object 46.

Starting from the embodiment according to FIG. 4, the inventive optical arrangement 20 or the inventive method can be changed in many ways. It is thus possible for the optical arrangement 20 to be integrated in a microscope to facilitate the handling of the optical arrangement 20. Instead of a spectroscopic examination of the material of the object 46, also a microscopic examination of the object 46 can then in particular be effected. It was already explained that, apart from an examination of an object 46, also a material processing of an object 46 is possible, for example two-photon polymerization of the material of the object 46 at the target position 49. In this case, the object 46 is a workpiece which can be located, for example, in an (optionally movable) object holder.

Particular advantages result with a variation of the settings or parameters of the optical arrangement 20. In the optical arrangement 20 shown in FIG. 4, it is, for example, very easily possible to sample a linear region within the object 46 by correspondingly changing the target position 49. To this end, the distance D of the mirror 38 in the delay line 37 is gradually changed. By this, the second laser pulses correspondingly arrive at the object 46 earlier or later, so that the target position 49 where the two laser pulses arrive simultaneously is correspondingly shifted to the right or to the left along the third path 43. For maintaining a high intensity at the target position 49, it would be recommendable for the two focusing optics 47, 48 to be moved along in a suitable manner to continue focusing the respective laser pulses to the target position 49 where the two laser pulses now arrive simultaneously. Scanning in one of the directions in space perpendicular to the adjustment direction of the two laser pulses can be done by correspondingly dislocating the object 46.

Figure 5:
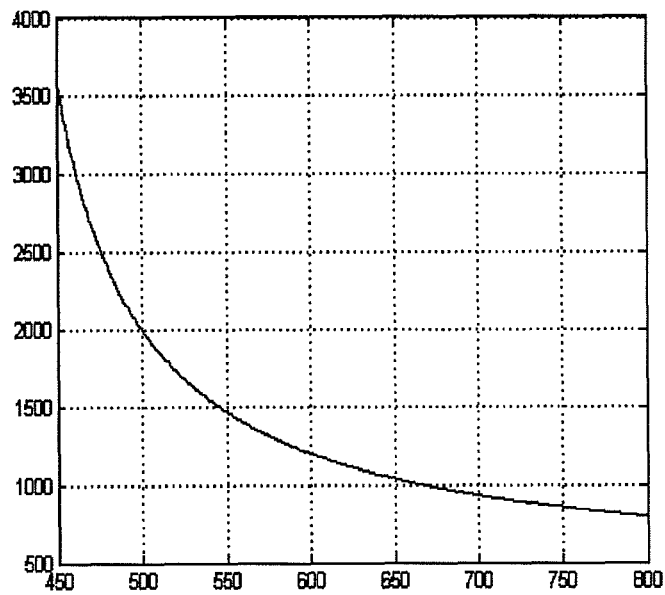

A further variation possibility (which is impossible with the conventional "degenerated" two-photon process) is presented by changing the central wavelength of one or two of the laser pulses. FIG. 5 shows by way of example different combination possibilities of the wavelengths of two photons to excite a one-photon transition at a wavelength of 400 nm by simultaneous absorption of both photons. Here, the Y-axis shows the wavelength of a photon which exactly supplies the missing energy for the 400 nm transition to a photon at a wavelength indicated on the X-axis (within a range of 450 nm to the "degenerated" situation at 800 nm). As combination possibilities, there are available, for example, photons with 500 and 2000 nm, with 550 and approximately 1450 nm, with 600 and 1250 nm, with 650 and 1080 nm, etc.

Figure 6:
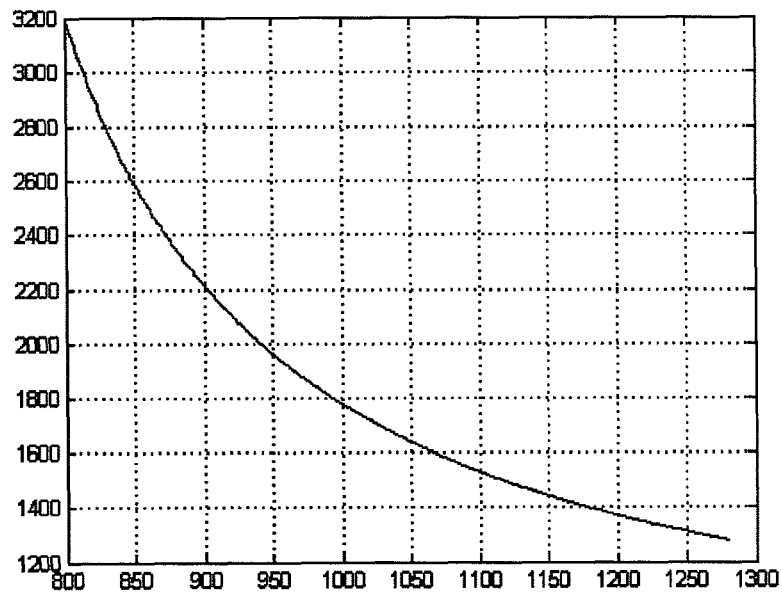

FIG. 6 shows an analogous diagram for combination possibilities of two photons for exciting a one-photon transition at 640 nm by means of the inventive not degenerated two-photon absorption. Possible wavelengths of the first photon of 800 nm up to the "degenerated" situation at 1280 nm not covered by the invention are represented on the X-axis, while corresponding wavelengths of the second photon are represented on the Y-axis.

For changing the central wavelength of the laser pulse generators 21, 22, these can each be tunable. This can be achieved by using, as the first laser pulse generator 21 and/or as the second laser pulse generator 22, an optical-parametric oscillator (OPO), or by the filters 24, 31 used in the laser pulse generators 21 having variable properties or being replaced by filters with other filter properties. The tuning of the first and/or second laser pulse in particular at a constant total energy permits the changing of the energy level E shown in FIG. 1, preferably continuously variably. Such a variation of the energy level E is not possible with the conventional "degenerated" two-photon processes. Changing the energy level E permits up to now unobtainable new findings on the material of the object 46 since the transition possibility can depend on the position of the energy level E relative to the intermediate level Z. By tuning the two laser pulses, consequently the intermediate levels Z can be determined. Moreover, the tuning of the energy level E permits the clear increase of the transition probability up to a value which approximately corresponds to that of a one-photon transition. This is also helpful for material processing as it decisively increases the efficiency of material processing.

As a variation of the optical arrangement 20 shown in FIGS. 3 and 4, two different ultra-short pulse lasers, each with different central wavelengths, could also be provided as laser pulse generators 21, 22. For example, the first laser pulse generator 21 could be an erbium-doped fiber laser, and the second laser pulse generator 22 an ytterbium-doped fiber laser.

In the optical arrangement 20 shown in FIGS. 3 and 4, the first laser pulse generator 21 comprises an (optional) optical amplifier 61, such as a fiber amplifier, in particular a variable amplifier, in order to increase the laser power. Further, the first laser pulse generator 21 comprises a dispersion controller 62 configured to control the pulse duration, and a pulse shaper 63. For the sake of available space in the drawing, the second laser pulse generator 22 is shown as comprising only an optical amplifier 61. However, the second laser pulse generator 22 may also have a dispersion controller 62 and/or a pulse shaper 63.

Figure 7:
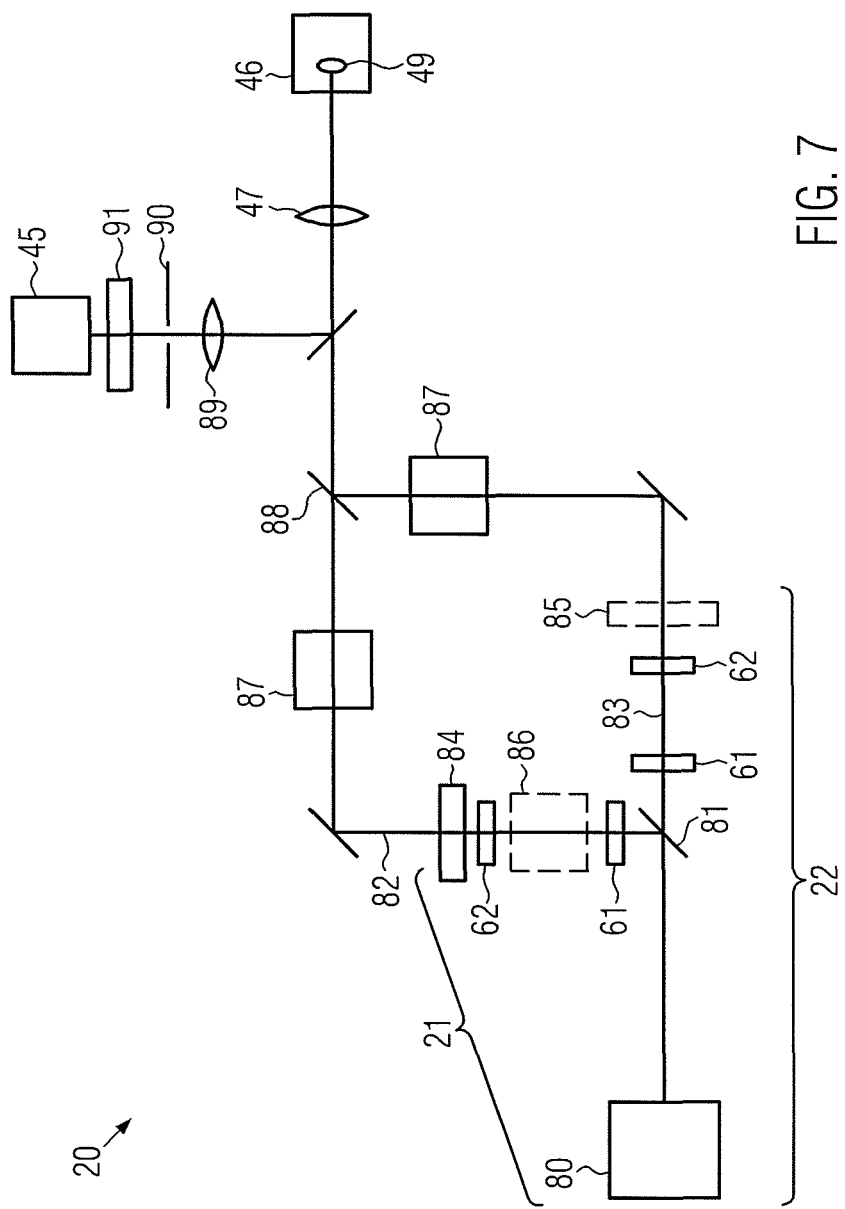

FIG. 7 schematically shows further variation possibilities of the optical arrangement 20 according to the invention. In the variant shown in FIG. 7, a common ultra-short pulse laser or frequency comb 80, or an erbium- or ytterbium-doped fiber laser 80, is provided both for the first laser pulse generator 21 and for the second laser pulse generator 22. The laser pulses exiting from the ultra-short pulse laser 80 are divided into a first path 82 and a second path 83 by a beam splitter 81. At the start of the two paths 82, 83, the two split laser pulses consequently have identical spectra. In the first path 82, however, there now is a filter 84 for filtering out a certain part from this spectrum and thus change the central wavelength of the laser pulse passing through the first path 82. Optionally, in the second path 83, too, an optionally different filter 85 could be provided for also changing the spectrum of the second laser pulse in view of its central wavelength. As an alternative, the spectrum of the first laser pulse could also remain unchanged in the second path 83. In a further alternative, in addition or as an alternative to the optical filter 48, there is an optical element 86 in the first path 82 which changes the central wavelength of the laser pulse for example by frequency duplication, frequency multiplication or by wavelength shifting, for example a Raman shift, so that the central wavelength of the laser pulse from the first laser pulse generator 21 differs from the central wavelength of the second laser pulse which is generated in the second laser pulse generator 22. Each of the two paths 82, 83 can furthermore have beam shaping elements or beam shapers 87, such as apertures or lens systems, and suitable amplifiers or attenuators for the respective laser radiation.

By means of a beam combiner 88, the laser pulses from the two paths 82, 83 are joined again. Preferably, the optical path lengths of the two paths 82, 83 are identical, so that the two laser pulses arrive at the beam combiner 88 simultaneously, though at different central wavelengths. By means of focusing optics 47, the two laser pulses are focused onto an identical target position 49 within the object 46. However, the two laser pulses do not need to be combined by a beam combiner 88. Instead, they could be arranged to reach the common target position under any mutual non-zero angle, or from opposite directions (such as shown in FIGS. 3 and 4).

FIG. 7 furthermore shows a detection of the fluorescent light emitted from the target position 49 by means of a detector 45. Here, detection optics 89 focus the fluorescent light onto a pin aperture 90 before this light reaches the detector 45. An optical filter 91 for letting pass only the signal emission can be optionally provided in the detection path of rays to improve the signal quality.

In the optical arrangement 20 shown in FIG. 7, the first laser pulse generator 21 comprises an (optional) optical amplifier 61, such as a fiber amplifier, in particular a variable amplifier, in order to increase the laser power. Further, the first laser pulse generator 21 comprises a dispersion controller 62 configured to control the pulse duration. The second laser pulse generator 22 is shown as comprising an optical amplifier 61, and a dispersion controller 62.

In each conceivable configuration, the optical arrangement 20 according to the invention can be a sampling or scanning device for sampling a one-, two- or three-dimensional region of the object 46 by changing the target position 49.

The invention claimed is:

1. An optical arrangement for examining or processing an object, comprising:
a first laser pulse generator for generating a first laser pulse with a first central wavelength,
a second laser pulse generator for generating a second laser pulse with a second central wavelength, wherein the second central wavelength is different from the first central wavelength,
a beam steering system which is configured to superimpose the first laser pulse and the second laser pulse at a certain target position within or on the object, so that multi-photon absorption takes place at the target position with the involvement of at least one photon of the first laser pulse and at least one photon of the second laser pulse,
wherein the first laser pulse generator and the second laser pulse generator each comprise a separate, pulsed laser, the two pulsed lasers are synchronized with each other, the first laser pulse generator comprises an erbium-doped fiber laser and the second laser pulse generator comprises a ytterbium-doped fiber laser.

2. The optical arrangement according to claim 1, wherein the first laser pulse and/or the second laser pulse is a sub-picosecond laser pulse.

3. The optical arrangement according to claim 1, wherein first focusing optics for focusing the first laser pulse to the target position, and/or second focusing optics for focusing the second laser pulse to the target position are provided.

4. The optical arrangement according to claim 1, wherein a detector is provided for detecting an emitted signal.

5. The optical arrangement according to claim 1, wherein the first laser pulse generator and/or the second laser pulse generator are/is tunable.

6. The optical arrangement according to claim 1, wherein the beam steering system is configured to entirely superimpose the first laser pulse and the second laser pulse at the target position.

7. The optical arrangement according to claim 1, wherein at least one variable beam shaper is provided in the path of the first laser pulse and/or of the second laser pulse.

8. The optical arrangement according to claim 1, wherein the first laser pulse and the second laser pulse only partially overlap at the target position.

9. The optical arrangement according to claim 8, wherein the spatial overlap of the first laser pulse and the second laser pulse at the target position is adjustable.

10. The optical arrangement according to claim 1, wherein the first central wavelength and the second central wavelength are variable while maintaining the sum of photon energies of a photon of the first laser pulse and a photon of the second laser pulse.

11. An optical arrangement for examining or processing an object, comprising:
a first laser pulse generator for generating a first laser pulse with a first central wavelength,
a second laser pulse generator for generating a second laser pulse with a second central wavelength, wherein the second central wavelength is different from the first central wavelength,
a beam steering system which is configured to superimpose the first laser pulse and the second laser pulse at a certain target position in or on the object, so that multi-photon absorption takes place at the target position with the involvement of at least one photon of the first laser pulse and at least one photon of the second laser pulse,
wherein a common pulsed laser is provided for the first laser pulse generator and the second laser pulse generator,
and wherein the common pulsed laser is a phase coherent light source and wherein the two laser pulse generators are configured to generate secondary first or second laser pulses, respectively, with different central wavelengths from primary laser pulses provided by the common pulsed laser, and the first laser pulse and the second laser pulse are configured to reach the target position under a non-zero mutual angle.

12. The optical arrangement according to claim 11, wherein the common pulsed laser is a frequency comb generator.

13. The optical arrangement according to claim 11, wherein the one laser pulse generator is configured to shift the central wavelength of a primary laser pulse from the common pulsed laser by a different amount than the other laser pulse generator.

14. The optical arrangement according to claim 11, wherein the one laser pulse generator is configured to filter out a spectral region with a different central wavelength from the spectrum of the pulsed laser than the other laser pulse generator.

15. The optical arrangement according to claim 11, wherein both laser pulse generators are implemented in a common path.

16. The optical arrangement according to claim 11, wherein the dispersion of at least one of the pulses is controlled so that control of the temporal overlap at the target is achieved.

17. The optical arrangement according to claim 11, wherein the first laser pulse and the second laser pulse are configured to reach the target position from exactly opposite directions.

18. The optical arrangement according to claim 11, wherein the first central wavelength and the second central wavelength are variable while maintaining the sum of photon energies of a photon of the first laser pulse and a photon of the second laser pulse.

19. A method of examining or processing an object, comprising the following steps:
- irradiating a first laser pulse with a first central wavelength into the object,
- irradiating a second laser pulse with a second central wavelength into the object, the second central wavelength being different from the first central wavelength,
- wherein the irradiation of the first laser pulse and the second laser pulse is done such that at a certain target position within or on the object, multi-photon absorption takes place with the involvement of at least one photon of the first laser pulse and at least one photon of the second laser pulse,
- the first and second laser pulses are generated either by means of two separate synchronized lasers, or by means of first and second laser pulse generators which generate secondary first or second laser pulses each with different central wavelengths from a primary laser pulse provided by a common pulsed laser, and
- one of the first central wavelength and the second central wavelength is increased and the other of the first central wavelength and the second central wavelength is decreased while maintaining the sum of photon energies of a photon at the first central wavelength and another photon at the second central wavelength.

20. The method according to claim 19, wherein the first laser pulse and/or the second laser pulse are/is a sub-picosecond laser pulse.

21. The method according to claim 19, wherein the first laser pulse and/or the second laser pulse are/is focused onto the target position.

22. The method according to claim 19, wherein a region of the object is sampled by changing the target position.

23. The method according to claim 19, wherein the first laser pulse and the second laser pulse reach the target position under a non-zero mutual angle.

24. The method according to claim 19, wherein the first laser pulse and the second laser pulse reach the target position from exactly opposition directions.

* * * * *